(12) United States Patent
Werner et al.

(10) Patent No.: US 7,217,814 B2
(45) Date of Patent: *May 15, 2007

(54) METHODS OF PRODUCING PHOSPHITYLATED COMPOUNDS

(75) Inventors: Christian Werner, Hannover (DE); Frank Nerenz, Hannover (DE); Andreas Kanschik-Conradsen, Garbsen (DE); Kalakota S. Reddy, Midland, MI (US)

(73) Assignee: Honeywell International Inc., Morristown, NJ (US)

( * ) Notice: Subject to any disclaimer, the term of this patent is extended or adjusted under 35 U.S.C. 154(b) by 61 days.

This patent is subject to a terminal disclaimer.

(21) Appl. No.: 10/990,138

(22) Filed: Nov. 16, 2004

(65) Prior Publication Data

US 2005/0124804 A1    Jun. 9, 2005

Related U.S. Application Data

(63) Continuation of application No. 10/373,336, filed on Feb. 24, 2003, now Pat. No. 6,894,158.

(60) Provisional application No. 60/362,320, filed on Mar. 7, 2002, provisional application No. 60/359,124, filed on Feb. 22, 2002.

(51) Int. Cl.
    C07H 21/00    (2006.01)
(52) U.S. Cl. .................................. 536/25.34
(58) Field of Classification Search .............. 536/25.34
    See application file for complete search history.

(56) References Cited

U.S. PATENT DOCUMENTS

| | | | |
|---|---|---|---|
| 4,725,677 A | 2/1988 | Köster et al. .................. 536/27 |
| 4,783,263 A * | 11/1988 | Trost et al. .................. 210/638 |
| 5,013,830 A | 5/1991 | Ohtsuka et al. ................ 536/27 |
| 6,274,725 B1 | 8/2001 | Sanghvi et al. .......... 536/25.34 |
| 6,340,749 B1 | 1/2002 | Zhang et al. ............ 536/25.34 |
| 6,506,894 B1 | 1/2003 | Reese et al. ............... 536/25.3 |
| 6,642,373 B2 * | 11/2003 | Manoharan et al. ..... 536/25.34 |
| 6,894,158 B2 * | 5/2005 | Werner et al. ........... 536/25.34 |

FOREIGN PATENT DOCUMENTS

SU        1196365 A  * 12/1985
WO    WO 98/16540      4/1998

OTHER PUBLICATIONS

[R] He et al., "Synthesis and Separation of Diastereomers of Ribonucleoside 5'-(_-P-Borano)triphosphates," Journal of Organic Chemistry, 63(17), 5769-5773 (Aug. 21, 1998).*
Applied BioSystems User's Manual for Models 392 and 394 DNA/RNA Synthesizers; Section 6 Chemistry for Automated DNA/RNA Synthesis (Mar. 1994) and M.J. Gait, "Oligonucleotide Synthesis, A Practical Approach", IRL Press at Oxfore University Press (1984), ISBN 0-904147-74-6.

Beaucage and Carruthers, "Deoxynucleoside Phosphoramidites—A New Class of Key Intermediates for Deoxypolynucleotide Synthesis," Tetrahedron Lett. 1981, 22, 1859.

Beier, Pfleiderer, "Nucleotides Part LXII, Pyridinium Salts—An Effective Class of Catalysts for Oligonucleotide Synthesis," Helvetica Chimica Acta, 1999, 82, 879.

Berner et al., "Studies on the role of tetrazole in the activation of phosphoramidities," Nucleic Acids Res. 1989, 17, 853.

Dahl, B., et al., "Mechanistic studies on the phosphoramidite coupling reaction in oligonucleotide synthesis," Nucleic Acids Res. 1987, 15, 1729.

Eleuteri, A., et al., "Pyridinium Trifluoracetae/N-Methylimidazole as an Efficient Activator for Oligonucleotide Synthesis via the Phosphoramidite Method," Organic Process Research & Development (2000), 4, 182-189.

Gryaznov, Letsinger, "Synthesis of oligonucleotides via monomers with unprotected bases," J Am. Chem. Soc. 1991, 113, 5876-5877.

Gryaznov, Letsinger, "Selective O-phosphitilation with nucleoside phosphoramidite reagents," Nucleic Acids Res. 1992, 20, 1879.

Hayakawa et al., "Acid/Azole Complexes as Highly Effective Promoters in the Synthesis of DNA andRNA Oligomers via the Phosphoramidite Method," J. Am. Chem. Soc., 2001, vol. 123; 34; pp. 8165-8176.

(Continued)

*Primary Examiner*—S. Anna Jiang
*Assistant Examiner*—L. E. Crane

(57) ABSTRACT

Provided are methods of producing phosphitylated compounds, including 3'-O-phosphoramidites, comprising the step of reacting a hydroxyl-containing compound with a phosphitylating agent in the presence of a phosphitylation activator selected from the group consisting of: (1) acid-base complexes derived from an amine base of Formula II

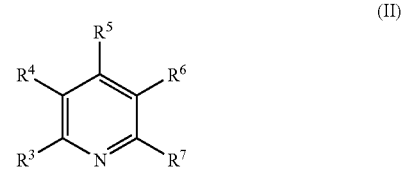

(II)

wherein $R^3$, $R^4$, $R^5$, $R^6$, and $R^7$ are independently hydrogen, $C_1$–$C_{10}$ alkyl, $C_3$–$C_{10}$ cycloalkyl, $C_6$–$C_{10}$ aryl, $C_7$–$C_{10}$ aralkyl, $C_1$–$C_{10}$ heteroalkyl, or $C_1$–$C_{10}$ heteroaryl, and at least one of $R^3$, $R^4$, $R^5$, $R^6$, and $R^7$ is not hydrogen; (2) zwitterionic amine complexes; and (3) combinations of two or more thereof, to produce a phosphitylated compound. Further provided are methods for purifying phosphitylated compounds comprising the steps of providing a phosphitylated compound in a solution solvent, contacting said phosphitylated compound with a precipitation solvent, and precipitating said phosphitylated compound.

23 Claims, No Drawings

OTHER PUBLICATIONS

Koster, et al., "β-Cyanoethyl N, N-Dialkylamino/N-Morpholinomonochloro Phosphoamidites, New Phosphitylating Agents Facilitating Ease of Deprotection and Work-up of Synthesized Oligonucleotides," Tetrahedron Lett. 24, 5843-5846 (1983).

Lee et al., Bis-(N,N-Dialkylamino)-Alkoxyphosphines as a New Class of Phosphite Coupling Agent for the Synthesis of Oligonucleotides,: Chem. Lett. 1229-1232 (1984).

McBride, et al., "Amidine Protecting Groups of Oligonucleotide Synthesis," J. Am. Chem. Soc., 1985, vol. 108, pp. 2040-2048.

Mellor, Thomas, "Synthesis of analogues of oligonucloetides", J. Chem Soc., Perkin Trans. 1, 1998, 747-757.

Nielsen et al., "Application of 2-cyanoethyl N,N,N',N'-tetraisopropylphosphorodiamidite for in situ preparation of deoxribonucleoside phosphoramidites and their use in polymer-supported synthesis of oligodeoxyribonucleotides," Nucleic Acids Res. 1986, 14, 7391-7403.

Noe and Kaufhold, "9 Chemistry of Antisense Oligonucleotides," New Trends in Synthetic Medicinal Chemistry, Wiley-VCh Weinheim, 2000, 261-347.

Pedersen, D., et al., "Preparation of LNA Phosphoramidites," Synthesis 2000, No. 6, (Apr. 29, 2002) pp. 802-808.

Sanghvi, et al., "Improved Process for the Preparation of Nucleosidic Phosphoramidites Using a Safer and Cheaper Activator," Organic Process Research and Development, 2000, 4, 175-181.

Sinha et al., "Polymer support oligonucleotide synthesis XVIII [1,2]; β-Cyanoethyl N, N-dialkylamino/N-Morpholinomo Phosphoamidite of deoxynucleosides for the synthesis of DNA fragments simplifying deprotection and isolation of the final product," Nucleic Acids Research, 4539-4557(1984), vol. 12 (11).

Sigma-Aldrich Chemie GmbH., "1H-Tetrazole, 99+%," MSDS, Catalog #243957, May 2003.

Stull, "Fudamentals of Fire and Explosion," AIChE Monograph Series, No. 10, New York, 1977, vol. 73, 22.

Zhaoda Zhang and Jin Yan Tang, Tetrahedron Letters, vol. 37, No. 3, pp. 331-334 (1996).

* cited by examiner

METHODS OF PRODUCING PHOSPHITYLATED COMPOUNDS

CROSS-REFERENCE TO RELATED APPLICATIONS

This application is a continuation of and claims priority to U.S. application Ser. No. 10/373,336, filed Feb. 24, 2003, granted as U.S. Pat. No. 6,894,158 on May 17, 2005, which in turn claims the priority of U.S. Provisional Application No. 60/359,124 filed Feb. 22, 2002, and of U.S. Provisional Application No. 60/362,320 filed Mar. 7, 2002. Each of the aforementioned applications are incorporated herein by reference.

FIELD OF THE INVENTION

The present invention is directed to methods of producing phosphitylated compounds by reacting a hydroxyl-containing compound with a phosphitylating agent in the presence of a phosphitylation activator.

BACKGROUND

The production of phosphitylated compounds via the reaction of hydroxyl-containing compounds with phosphine reagents is a transformation that has found utility in the synthesis of a wide range of useful compounds. For example, applicants have recognized that such a transformation is useful in the synthesis of 3'-O-phosphoramidites from 5'-O-protected nucleosides, as shown generally in Scheme 1:

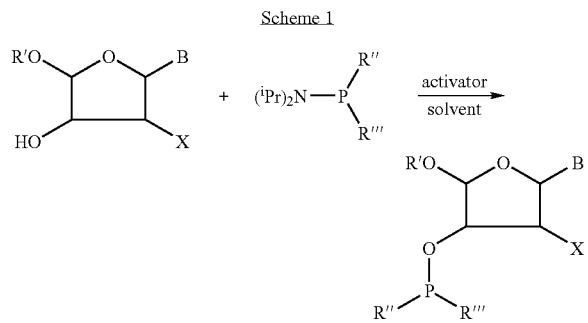

wherein, for example, X is hydrogen, alkoxy, —O-tert-butyldimethyl silyl (OTBDMS), —O-methoxy methyl (OMOM), 2'-O-methoxyethyl (2'-O-MOE), and the like; R' is DMT, dimethoxytrityl, oligonucleotides and analogs thereof, and the like; R" is alkyl, such as methyl and the like, or alkoxy, such as 2-cyanoethyl and the like; R'" is diisopropylamine and the like; and B is moiety derived from adenine, cytosine, guanine, thymine, or uracil.

Phosphoramidites of the type formed via Scheme 1 can be advantageously coupled to prepare oligonucleotides, see for example U.S. Pat. No. 4,725,677 and Mellor, Thomas, "Synthesis of analogues of oligonucloetides", *J. Chem Soc., Perkin Trans.* 1, 1998, 747–757 (both of which are incorporated herein by reference), which have a rising importance in the field of therapeutic and diagnostic applications including, for example, antisense drugs (as described in Crooke, S. T. *Handbook of Experimental Pharmacology: Antisense Research and Application*; Springer-Verlag, Berlin, (1998), incorporated herein by reference). To supply the growing demand for these oligonucleotides, there is a desire to improve the synthesis of nucleosidic phosphoramidites on a commercial scale (Noe, Kaufhold, *New Trends in Synthetic Medicinal Chemistry*, Wiley-VCh Weinheim, 2000, 261, incorporated herein by reference).

However, applicants have come to appreciate that conventional methods for preparing phosphitylated compounds, such as 3'-O-phosphoramidites, from hydroxyl-containing compounds are disadvantageous for several reasons. One disadvantage associated with many conventional methods is the required use of costly and/or hazardous activating agents/compounds. For example, in Beaucage and Carruthers, *Tetrahedron Lett.* 1981, 22, 1859 (incorporated herein by reference), 1H-Tetrazole is recommended as the most versatile phosphitylation activator. However, such an activator/reagent is both expensive and hazardous. (See, for example, Stull, *Fundamentals of Fire and Explosion*, AlChE Monograph Series, No. 10, New York, 1977, Vol. 73, 22, incorporated herein by reference). Due to the explosive nature of the nitrogen-rich heterocycle, special safety precautions are required for the handling of such composition. A less hazardous compound, 4,5-Dicyanoimidazole, has been shown to be useful in the production of certain nucleosidic phosphoramidites. Unfortunately, this compound is very expensive, and, in fact, tends to be prohibitively expensive with regard to its use in industrial processes. Phosphitylation activators derived from unsubstituted pyridine are disclosed, for example, in Gryaznov, Letsinger, *J. Am. Chem. Soc.* 1991, 113, 5876; Gryaznov, Letsinger, *Nucleic Acids Res.* 1992, 20, 1879; Beier, Pfleiderer, *Helvetica Chimica Acta*, 1999, 82, 879; Sanghvi, et al., *Organic Process Research and Development* 2000, 4, 175; and U.S. Pat. No. 6,274,725, issued to Sanghvi et al., all of which are incorporated herein by reference. However, these salts tend to be toxic and highly water soluble. Accordingly, cost-intensive waste water treatment equipment must be installed in systems using such activators.

Another disadvantage associated with many conventional methods for preparing phosphitylated compounds is the use of dichloromethane as the preferred solvent. Because dichloromethane tends to be environmentally unfriendly, relatively costly waste treatment equipment is required for use in conjunction with methods involving dichloromethane as solvent.

One potential approach to avoid at least some of the aforementioned disadvantages is in situ preparation of nucleosidic phosphoramidites without an additional activation step, as described, for example, by Zhang et al., U.S. Pat. No. 6,340,749 B1, for immediate use of the resulting solution on the solid support synthesizer. Unfortunately, such methods tend to be relatively inefficient, and the phosphoramidite solutions obtained via such methods tend to be unstable and unsuitable for storage.

Accordingly, applicants have recognized the need for new methods of producing phosphitylated compounds which avoid the disadvantages associated with conventional methods.

DESCRIPTION OF THE INVENTION AND PREFERRED EMBODIMENTS

The present invention overcomes the aforementioned shortcomings by providing efficient methods of producing a wide variety of phosphitylated compounds, which methods tend to be less hazardous and less costly than conventional methods. Specifically, applicants have discovered that certain acid-base complexes and zwitterionic complexes derived from relatively sterically-hindered amine bases can be used to great advantage as phosphitylation activators in methods of preparing phosphitylated compounds from hydroxyl-containing starting materials. As used herein, the term "phosphitylated compound" refers generally to a compound containing an oxygen-phosphorus bond formed via the reaction of a hydroxyl-containing compound with a phosphitylating agent. Applicants have discovered that acid-base and zwitterionic complexes of the present invention tend to be both less toxic and less water soluble than conventional activators.

In addition, applicants have discovered unexpectedly that, in many embodiments, the methods of the present invention allow for the production of phosphitylated compounds in yields at least as high, and in certain cases, higher than those achieved via prior art processes despite the fact that the acid-base and zwitterionic activator complexes of the present invention tend to be more sterically-hindered, and less nucleophilic, than activators used conventionally. Although applicants do not wish to be bound by or to any particular theory of operation, it is believed that the mechanism of activating a phosphitylating agent for use in the production of phosphitylated compounds involves the nucleophilic displacement of a leaving group on the phosphitylating agent by the activator. For example, Berner et al. *Nucleic Acids Res.* 1989, 17, 853 and Dahl, B., et al., *Nucleic Acids Res.* 1987, 15, 1729 describe the proposed mechanism of activation of the bis-reagent 2-cyanoethyl-N,N,N',N'-tetraisopropylphosphoramidite with a less-sterically hindered amine activators (such as tetrazole) as involving the displacement of a diisopropylamine leaving group by the nucleophilic amine, prior to the reaction of the activated bis-reagent agent with a hydroxyl-containing compound.

In light of this, it would be expected that the present activators comprising amines that are relatively, and in many cases significantly, more sterically-hindered than prior art amine activators, such as tetrazole and pyridine activators, would be less efficient in displacing leaving groups on phosphitylating agents, and therefor less efficient in activating such agents to produce phosphitylated compounds. Nevertheless, as noted above, applicants have found, surprisingly, that significantly sterically-hindered activators of the present invention allow for the production of phosphitylated products in yields as good or even better than conventional activators, such as the salts of unsubstituted pyridine. Without intending to be bound by or to any particular theory of operation, subsequent investigation into the discovered unexpected results has lead applicants to believe that the surprisingly high yields associated with present activators may be due, at least in part, to reduced side reactions of the activator with reactive moieties of certain hydroxyl-containing starting materials (e.g. the lactam unit of guanosine compounds as discussed by Nielsen et al. *Nucleic Acids Res.* 1986, 14, 7391.) Accordingly, the present methods allow for the production of phosphitylated compounds in yields as good as, and often better, than conventional methods while also avoiding many of the disadvantages associated with such conventional methods.

According to certain embodiments, the methods of the present invention comprise the step of reacting a hydroxyl-containing compound with a phosphitylating agent in the presence of a phosphitylation activator selected from the group consisting of: acid-base complexes derived from amines of Formula I or Formula II, described below, acid-base complexes derived from diazabicyclo amine compounds, zwitterionic amine complexes, and combinations of two or more thereof, to produce a phosphitylated compound.

Phosphitylation Activator

As used herein the term "phosphitylation activator" refers generally to a compound that promotes the reaction of a hydroxyl-containing compound with a phosphitylating agent to produce a phosphitylated compound according to the present invention. Applicants have discovered that a wide range of acid-base complexes and zwitterion complexes can be used to great advantage as phosphitylation activators.

I. Acid-Base Complexes

The complexes of acids and bases of the present invention are formed by introducing at least one amine base of Formula I or Formula II, described below, or a diazabicyclo amine base, to at least one acid to form an acid-base complex.

wherein R, $R^1$, and $R^2$ are independently $C_1$–$C_{10}$ alkyl, $C_3$–$C_{10}$ cycloalkyl, $C_6$–$C_{10}$ aryl, $C_7$–$C_{10}$ aralkyl, $C_1$–$C_{10}$ heteroalkyl, or $C_1$–$C_{10}$ heteroaryl;

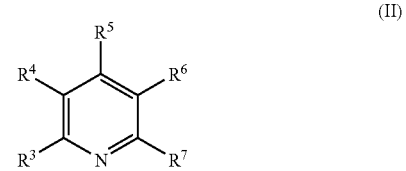

wherein $R^3$, $R^4$, $R^5$, $R^6$, and $R^7$ are independently hydrogen, $C_1$–$C_{10}$ alkyl, $C_3$–$C_{10}$ cycloalkyl, $C_6$–$C_{10}$ aryl, $C_7$–$C_{10}$ aralkyl, $C_1$–$C_{10}$ heteroalkyl, or $C_1$–$C_{10}$ heteroaryl, wherein at least one of $R^3$, $R^4$, $R^5$, $R^6$, and $R^7$ is not hydrogen.

R, $R^1$, $R^2$, $R^3$, $R^4$, $R^5$, $R^6$, and $R^7$ as $C_1$ to $C_{10}$ alkyl groups may be straight chain or branched moieties, for example, substituted or unsubstituted: methyl, ethyl, n-propyl, isopropyl, n-butyl, isobutyl, tert-butyl, n-pentyl, neopentyl, n-hexyl, n-heptyl, n-octyl, 2-ethylhexyl, nonyl, decyl and the like. Any of these groups may be substituted with halogen, hydroxyl, alkoxy, aryloxy, alkyl, fluoroalkyl, arylalkyl groups, and the like.

R, $R^1$, $R^2$, $R^3$, $R^4$, $R^5$, $R^6$, and $R^7$ as $C_3$ to $C_{10}$ cycloalkyls may be, for example, substituted or unsubstituted: cyclopropyl, cyclobutyl, cyclopentyl, methylcyclopentyl, cyclohexyl, methylcyclohexyl, dimethylcyclohexyl, cycloheptyl, cyclooctyl, and the like. Any of these groups may be substituted with, for example, halogen, hydroxyl, alkoxy, aryloxy, alkyl, fluoroalkyl, arylalkyl groups, and the like.

R, $R^1$, $R^2$, $R^3$, $R^4$, $R^5$, $R^6$, and $R^7$ as $C_6$ to $C_{10}$ aryls may be, for example, substituted or unsubstituted: phenyl, o-tolyl, m-tolyl, p-tolyl, o-xylyl, m-xylyl, p-xylyl, alpha-naphthyl, beta naphthyl, and the like. Any of these groups may be substituted with, for example, halogen, hydroxyl, aryloxy, alkyl, fluoroalkyl, arylalkyl groups, and the like.

R, $R^1$, $R^2$, $R^3$, $R^4$, $R^5$, $R^6$, and $R^7$ as $C_7$ to $C_{10}$ aralkyls may be, for example, substituted or unsubstituted: benzyl, 4-methylbenzyl, o-methylbenzyl, p-methylbenzyl, diphenylmethyl, 2-phenylethyl, 2-phenylpropyl, 3-phenylpropyl, and the like. Any of these groups may be substituted with, for example, halogen, hydroxyl, aryloxy, alkyl, fluoroalkyl, arylalkyl groups, and the like.

Any two adjacent R, $R^1$, and $R^2$, or $R^3$, $R^4$, $R^5$, $R^6$, and $R^7$ groups in Formulae I and II, respectively, may be connected to form an aromatic, non-aromatic, or heterocyclic ring.

Examples of amine bases of Formula I suitable for use in the present methods include: trialkylamines, such as, diisopropylethylamine (i.e. Hünig's Base), tripropylamine, triethylamine, trimethylamine, diethylmethylamine, N-methylmorpholine (NMM) and the like; tertiary diamines, such as, tetramethylethylendiamine (TMEDA); polyamines and polymer bound alkylamines; triarylamines, such as, triphenylamine, and the like; triaralkylamines, such as, tribenzylamine, and the like; other trisubstituted amines, such as dimethylaniline; and the like. Certain preferred amine bases of Formula I include Hünig's Base, and the like.

Examples of amine bases of Formula II suitable for use in the present methods include: dimethylaminopyridine (DMAP), 4-dimethylaminopyridine, and other substituted pyridines, such as, monoalkylpyridines, including methylpyridine, 2-picoline, 3-picoline, dialkylpyridines, including dimethylpyridine, 2,6-lutidine, trialkylpyridines, including trimethylpyridine, sym-collidine, tetraalkylpyridines, including tetramethylpyridine, and pentaalkylpyridines, including pentamethylpyridine, and the like. Certain preferred bases of Formula II include 2-picoline, sym-collidine, and the like.

Examples of diazabicyclo amine bases suitable for use in the present methods include 1,5-diazabicyclo[4.3.0]non-5-ene (DBN); 1,8-diazabicyclo[5.4.0]undec-7-ene (DBU); 1,1,3,3-tetramethylguanidine; and the like.

Any of a wide range of acids may be combined with one or more bases of the present invention to form an acid-base complex of the present invention. Suitable acids include: acetic acid derivaties, such as, trifluoroacetic acid (TFA), dichloroacetic acid, and the like; sulfonic acids, such as, methane sulfonic acid, trifluoromethane sulfonic acid, 4-pyridiniumethylene sulfonic acid, and the like, non-aqueous hydrogen halide acids, such as, non-aqueous hydrogen chloride, non-aqueous hydrogen bromide, non-aqueous hydrogen iodide, and the like; and $HBF_4$. In certain preferred embodiments, the acid used in the present invention is trifluoroacetic acid.

Certain preferred acid-base complexes of the present invention include complexes of: trifluoroacetic acid and Hünig's Base; trifluoroacetic acid and 2-picoline; and trifluoroacetic acid and sym-collidine. An especially preferred acid-base complex is a complex of trifluoroacetic acid and Hünig's Base.

Any of a wide range of known methods for forming acid-base complexes can be adapted for use in making acid-base complexes according to the present invention. For example, in certain embodiments, the present acid-base complexes are produced by introducing at least one acid to at least one base to form the complex.

The acids and bases of the present invention may be introduced in the presence or absence of solvent to form the present complexes. In embodiments including the presence of solvent, either or both of the acid and/or base may be first dissolved in solvent to form an acid solution and/or base solution, prior to contacting the acid and base to form the complex. The solvent used in forming an acid-base complex of the present invention may be the same or different from any optional solvent used in the phosphitylation reaction of the present invention. Solvents suitable for use in making an acid-base complex according to the present invention include non-polar and polar, aprotic solvents. Examples of suitable non-polar and polar, aprotic solvents include: acetates, such as, methyl acetate, ethyl acetate, propyl acetate, isopropyl acetate, n-butyl acetate, isobutyl acetate, and the like; ethers, such as, tetrahydrofuran (THF), methyl tert-butyl ether (MTBE), and the like; aromatic solvents, such as, toluene, chlorobenzene, and the like; dichloromethane; acetonitrile; N-methyl-2-pyrrolidone (NMP); N,N-dimethylformamide (DMF) and combinations of two or more of these. In certain embodiments, the base of the acid-base complex, or the complex itself may act as solvent.

Any suitable amounts of acid and base can be used in preparing the present acid-base complexes. In general, sufficient acid and base should be used such that the acid and base components are present in the complex in a molar ration of about 1:1. In certain embodiments, from about 0.9 to about 1.5 equivalents of base and from about 0.9 to about 1.5 equivalents of acid are used. Preferably, from about 0.9 to about 1.3 equivalents of base and from about 0.9 to about 1.1 equivalents of acid are used, and even more preferably from about 1.0 to about 1.3 equivalents of base and from about 1.0 to about 1.05 equivalents of acid are used. In certain especially preferred embodiments, about 1.3 equivalents of base and about 1.05 equivalents of acid are used. Unless otherwise indicated, all equivalents are molar equivalents.

The acid-base complexes of the present invention may be formed in situ in the phosphitylation reactions of the present invention, or may be formed separately therefrom. In embodiments wherein the complex is formed in situ, the complex may be formed in the reaction mixture prior to adding either the phosphine and/or hydroxyl-containing compound. Alternatively, the complex may be prepared after introduction of both the phosphine and/or hydroxyl-containing compounds to the reaction mixture by a subsequent addition of the acid and/or base of the complex.

Any suitable reaction conditions may be used to form the complexes of the present invention. For example, in certain embodiments, the acids and bases of the present invention are mixed at a temperature of from about 0° C. to about 100° C. Preferably, the acids and bases are mixed at a temperature of from about 10° C. to about 60° C., and more preferably from about 15° C. to about 40° C.

B. Zwitterion Complexes

As used herein, the term "zwitterion complex" refers generally to a complex ion having a cation and an anion in the same molecule (i.e. an internal salt), as is known in the art. Applicants have discovered unexpectedly that such zwitterion complexes are suitable for use as phosphitylation activators according to the present invention.

Any of a wide range zwitterionic compounds/internal salts are suitable for use according to the present invention. Examples of suitable zwitterionic compounds include sulfonic acid compounds, such as, pyridineethansulfonic acid, and the like.

Phosphitylating Agent

As used herein, the term "phosphitylating agent" refers generally to any reagent compound capable of reacting with a hydroxyl-containing compound in the presence of a phosphitylation activator to form a bond between the oxygen atom of a hydroxyl group of the hydroxyl-containing compound and a phosphorus atom of the phosphitylating agent to form a phosphitylated compound. Any of a wide range of compounds are suitable for use as phosphitylating agents according to the present invention. Suitable compounds include, for example, phosphines, such as bis-substituted phosphines, including, alkoxy-bis(dialkylamino)phosphines, such as bis-diisopropylamino-2-cyanoethoxyphosphine; dialkoxy(dialkylamino)phosphines; alkoxy-alkyl(dialkylamino)phosphines, bis(N,N-diisopropylamino)-2-methyltrifluoroacetylaminoethoxyphosphine; bis(N,N-diisopropylamino)-2-diphenyl-methylsilylethoxyphosphine; (allyloxy)bis(N,N-dimethylamino)-phosphine; and the like; as well as, phosphoramidites, such as, hydroxyl-protected-N,N,N',N'-phosphoramidites, including, 2-cyanoethyl-N,N,N',N-tetraisopropylphosphorodiamidite; methoxy-N,N,N',N'-tetraisopropylphosphorodiamidite; methyl-N,N,N',N'-tetraisopropylphosphorodiamidite, and the like, and 3'-O-phosphoramidites, such as, 5'-O-Dimethoxytrityl-2'-deoxyAdenosine($N^6$-Benzoyl)-3'-N,N-diisopropylamino-O-(2-cyanoethyl)phosphoramidite, 5'-O-Dimethoxytrityl-2'-($N^4$-Benzoyl)-3'-N,N-diisopropylamino-O-(2-cyanoethyl)phosphoramidite, 5'-O-Dimethoxytrityl-2'-deoxyGuanosine($N^2$-isobutyroyl)-3'-N,N-diisopropylamino-O-(2-cyanoethyl)phosphoramidite, 5'-O-Dimethoxytrityl-thymidine-3'-N,N-diisopropylamino-O-(2-cyanoethyl) phosphoramidite, and the like; and mixtures of two or more thereof. Preferred phosphitylating agents include hydroxyl-protected-N,N,N',N'-phosphoramidites, such as, 2-cyanoethyl-N,N,N',N'-tetraisopropylphosphorodiamidite, methoxy-N,N,N',N'-tetraisopropylphosphorodiamidite, 5'-O-Dimethoxytrityl-2'-deoxyAdenosine($N^6$-Benzoyl)-3'-N,N-diisopropylamino-O-(2-cyanoethyl)phosphoramidite, 5'-O-Dimethoxytrityl-2'-($N^4$-Benzoyl)-3'-N,N-diisopropylamino-O-(2-cyanoethyl)phosphoramidite, 5'-O-Dimethoxytrityl-2'-deoxyGuanosine($N^2$-isobutyroyl)-3'-N,N-diisopropylamino-O-(2-cyanoethyl)phosphoramidite, and 5'-O-Dimethoxytrityl-thymidine-3'-N,N-diisopropylamino-O-(2-cyanoethyl)phosphoramidite. In a particularly preferred embodiment, the phosphitylating agent is 2-cyanoethyl-N,N,N',N'-tetraisopropylphosphorodiamidite.

Hydroxyl-Containing Compounds

As used herein, the term "hydroxyl-containing compound" refers generally to a compound containing at least one hydroxyl group, which is capable of reacting with a phosphitylating agent in the presence of a phosphitylation activator to form a bond between an oxygen atom of at least one hydroxyl group of the hydroxyl-containing compound and a phosphorus atom of the phosphitylating agent to form a phosphitylated compound. In general, any compound comprising at least one hydroxyl group which is capable of reacting with a phosphitylating agent in the presence of a phosphitylation activator to form a bond between an oxygen atom of at least one hydroxyl group of the hydroxyl-containing compound and a phosphorus atom of the phosphitylating agent to form a phosphitylated compound is suitable for use as hydroxyl-containing compounds according to the present invention. In certain preferred embodiments, the hydroxyl containing compounds of the present invention include any natural and/or non-natural nucleosides, including DNA and/or RNA nucleosides, including Locked Nucleic Acid (LNA) derivatives and nucleosides substituted with additional groups, e.g. halogen substituents, Detector-containing nucleosides, including Biotin- or Fluorescein-linked compounds; Effector-containing compounds with ligands enhancing antisense action; as well as oligomeric structures derived from two or more of these. Examples of suitable DNA and RNA nucleosides include protected nucleosides, such as 5'-O-protected nucleosides (with or without additional N-protection, such as protection via benzoyl, isobutyryl, tert-butylphenoxyacetyl "TAC", and the like), including 5'-O-protected nucleosides of Adenosine, Cytidine, Guanosine, Thymidine, deoxyAdenosine, deoxyCytidine, and deoxyGuanosine; 5'-O-protected-2'-protected nucleosides, (with or without additional N-protection), including 5'-O-protected-2'-protected nucleosides of Adenosine, Cytidine, Guanosine, and Uridine (wherein preferred 2'-protecting groups include t-butyldimethylsilyl, methoxymethyl (MOM), methoxyethyl (MOE) and alkoxy, such as, methoxy, groups), as well as 3'-O-protected nucleosides of Adenosine, Cytidine, Guanosine, Thymidine, Uridine, deoxyAdenosine, deoxyCytidine, and deoxyGuanosine, (with or without additional N-protection) and oligomeric structures derived therefrom.

Reaction Solvent and Conditions

The present methods may be adapted for use as batch or continuous processes.

According to certain embodiments, the reaction step of the present phosphitylation methods further comprises a solvent. The solvent used in the phosphitylation reactions of the present invention may be the same or different from any optional solvent used in forming an acid-base complex of the present invention. Solvents suitable for use in the phosphitylation reaction according to the present invention include non-polar and polar, aprotic solvents. Examples of suitable non-polar and polar, aprotic solvents include: acetates, such as, methyl acetate, ethyl acetate, propyl acetate, isopropyl acetate, n-butyl acetate, isobutyl acetate, and the like; ethers, such as, THF, MTBE, and the like; aromatic solvents, such as, toluene, chlorobenzene, and the like; dichloromethane; acetonitrile; NMP; DMF and combinations of two or more of these. In certain embodiments, the base of the acid-base complex, or the complex itself may act as solvent.

Any suitable amounts of hydroxyl-containing compound and phosphitylating agent can be used in the methods of the present invention. In certain embodiments, from about 0.9 to about 1.5 equivalents of hydroxyl-containing and from about 0.9 to about 1.5 equivalents of phosphitylating agent are used. Preferably, from about 0.9 to about 1.1 equivalents of hydroxyl-containing compound and from about 0.9 to about 1.3 equivalents of phosphitylating agent are used, and even more preferably from about 0.9 to about 1.1 equivalents of hydroxyl-containing compound and from about 1.0 to about 1.3 equivalents of phosphitylating agent are used. In certain especially preferred embodiments, about 1.0 equivalents of hydroxyl-containing compound and about 1.1 equivalents of phosphitylating agent are used. Unless otherwise indicated, all equivalents are molar equivalents.

Any suitable reaction conditions, including conditions disclosed in any of the documents incorporated herein by reference, may be used in the phosphitylation reactions of the present invention. In certain embodiments, the phosphitylation reaction is conducted at a temperature of from about 0° C. to about 100° C. Preferably, the phosphitylation reaction is conducted at a temperature of from about 0° C. to about 40° C., and more preferably at about 20° C.

The phosphitylated compounds prepared via the present methods may be purified via any suitable methods known in the art. For example, aqueous washes, drying, concentrating under reduced pressure, chromatography, distillation, crystallization, precipitation and the like may be used.

According to certain preferred embodiments, applicants have discovered that relatively-highly pure phosphitylated compounds, such as, 3'-O-phosphoramidites, can be obtained by precipitating the phosphitylated compound in solution. In certain preferred embodiments, the precipitation methods of the present invention comprise providing a compound solution comprising a phosphitylated compound to be precipitated and a solvent, and contacting said compound solution with a precipitation solvent to precipitate the phosphitylated compound.

Any of a wide range of suitable solvents can be used in the compound solutions according to the present invention. Examples of suitable compound solution solvents include: toluene, xylene, methylacetate, ethylacetate, propylacetate, butylacetate, combinations of two or more thereof, and the like. Preferred compound solution solvents include toluene and the like.

The compound solutions can be provided via any of a wide range of methods according to the present invention. In certain preferred embodiments, the compound solution is provided as the product of a phosphitylation reaction of the present invention. Such solution may be obtained directly from the phosphitylation reaction or may be provided by purifying a reaction product and solvating such purified product. Alternatively, a phosphitylated compound obtained via a source other than a reaction of the present invention can be dissolved in a compound solution solvent to provide a compound solution according to the present invention.

Any suitable precipitation solvent can be used to precipitate phosphitylated compounds according to the present invention including alkanes, such as, petroleum ether, pentane, hexane, isohexane, heptane, isooctane, and the like, and mixtures of two or more thereof. Preferred precipitation solvents include petroleum ether, hexane, mixtures of two or more thereof, and the like.

In certain preferred embodiments, one or more additives can be added to the precipitation solvent to influence the structure of the precipitate in methods of the present invention. Examples of suitable additives include, for example, triethylamine, and the like. Any suitable amount of additive can be added to a precipitation solvent according to the present invention. In certain preferred embodiments, from about 0 to about 10% by weight, based on the total weight of precipitation solvent and additive, of additive is used, preferably from about 0 to about 5% is used.

Any suitable ratio of compound solution to precipitation solvent/additives can be used according to the present methods. In certain preferred embodiments, the compound solution is added to about 5 to about 25 equivalents by weight, preferably about 20 to about 25 equivalents, of precipitation solvent or precipitation solvent and additive (if present).

The precipitation can be conducted under any suitable conditions and using any suitable laboratory equipment. Preferably the precipitation is conducted under an inert gas atmosphere, such as nitrogen, argon, or the like. Any suitable temperature can be used, for example, from about −20° C. to about 40° C. Preferably, precipitation is conducted at a temperature of from about 0° C. to about 30° C., and more preferably, from about 5° C. to about 25° C. Any suitable vessels can be used for precipitation. In certain preferred embodiments, stainless steel vessels are used.

Automated Oligonucleotide Synthesis

As will be recognized by those of skill in the art, oligonucleotides may be synthesized from hydroxyl-containing compounds comprising nucleosides and/or oligomers derived therefrom according to the present methods, not only via the batch and/or continuous processes described above, but also using automated oligonucleotide synthesis techniques, as described, for example, in Applied BioSystems User's Manual for Models 392 and 394 DNA/RNA Synthesizers; Section 6 Chemistry for Automated DNA/RNA Synthesis (March 1994) and M. J. Gait, "Oligonucleotide Synthesis, A Practical Approach", IRL Press at Oxford University Press (1984, ISBN 0-904147-74-6), which are incorporated herein by reference. In such embodiments, a nucleoside and/or oligonucleotide hydroxyl-containing compound is immobilized on a solid support and reacted within an automated DNA Synthesizer with a nucleoside phosphitylating agent in the presence of a phosphitylation activator to form an oligonucleotide. A specified number and sequence of phosphitylation reactions may be conducted to produce oligonucleotides comprising different lengths and sequences of nucleosides according to the present invention.

Any suitable solid support materials may be adapted for use in the present invention. Examples of suitable solid support materials include controlled-pore glass ("CPG"), polystyrene, silica, cellulose paper, and combinations of two or more thereof. A preferred class of solid support material includes controlled-pore glass, polystyrene, and combinations thereof.

The solid support for use in the present methods may have pores of any suitable size. As will be recognized by those of skill in the art, the choice of pore size depends at least in part upon the size of the oligomer to be produced and the nucleotide synthesis procedure used. In light of the teachings herein, those of skill in the art will be readily able to select a solid support material of appropriate pore size for use in a wide variety of applications.

A variety of solid-support immobilized nucleosides are available commerically. For example, a number of n-protected deoxynucleosides immobilized on CPG (including 0.2 micromolar Benzoyl-protected deoxycytosine on 1000 angstrom CPG) are available from Applied Biosystems (ABI).

Any of a wide range of Automated DNA/RNA Synthesizers can be adapted for use in the present invention. Examples of suitable DNA Synthesizers include the Model Nos. 3900, 380, 380B, 392 and 394, Expedite 8800, 8905, 8909, Gene Assembler, OligoPilot, OligoPilot II, AKTAoligopilot 10, and AKTAoligopilot 100 available from Applied Biosystems, as well as, Beckmann Oligo 1000 and 1000M, the MWG Biotech Oligo 2000, PolyPlex GeneMachine, Illumina Oligator, MerMade I and II, Intelligent BioInstruments Primer Station 960, Proligo Polygen, Syntower, and the like. A preferred class of Synthesizer includes Model 394, and the like.

Any suitable amounts of solid-supported hydroxyl-containing compound and phosphitylating agent may be used according to the present automated methods. In certain preferred embodiments, an excess, preferably a fifty fold excess, of phosphitylating agent is used for each reaction.

EXAMPLES

The invention is further described in light of the following examples which are intended to be illustrative but not limiting in any manner.

Examples 1–11

These Examples illustrate the phosphitylation of several protected nucleoside reagents with 2-Cyanoethyl-N,N,N',N'-tetraisopropylphosphordiamidite in the presence of several activators according to the present invention.

Eleven phosphitylation reactions (1–11) comprising reacting a protected nucleoside reagent with 2-Cyanoethyl-N,N,N',N'-tetraisopropylphosphordiamidite in the presence of an acid-base activator according to the present invention were conducted, and the product yields of each calculated, as described in the General Procedure, below. The various combinations of protected nucleoside, activator base, activator acid, solvent, and yield for each of the 11 reactions are listed in Table 1.

General Procedure: The activator base (1.1 to 1.2 equivalents) is added to the solvent and 0.95 to 1.1 equivalents of activator acid is subsequently added thereto at ambient temperature to form the activator solution. About 1 equivalent of the protected nucleoside is dissolved in about 10 equivalents of the solvent in a separate vessel and about 3 equivalents of the solvent is then distilled off under reduced pressure. About 1 to 1.2 equivalents of 2-Cyanoethyl-N,N,N',N'-tetraisopropylphosphordiamidite is added to the nucleoside mixture at ambient temperature, and the activator solution prepared previously is then added to the nucleoside mixture at ambient temperature with vigorous stirring. After 12 hours, the reaction mixture is diluted with toluene and washed with water. The organic layer is separated, dried over sodium sulfate if necessary, and concentrated under reduced pressure. The yield of the desired amidite is then calculated using HPLC techniques, that is, the resulting product mixture is run through an HPLC column using an appropriate eluent, and the area under the HPLC peaks used to determine the % yield of product in the mixture.

and washed with petroleum ether. The product is then dried, weighed, and the percent yield calculated.

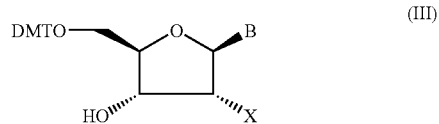

(III)

wherein B is a moiety derived from $N^6$-benzoyl-Adenine (A(Bz)), $N^4$-benzoyl-Cytisine (C(Bz)), $N^2$-isobutyroyl-Guanine (G(iBu)), Thymine (T), or Uracil (U), and X is hydrogen, OTBDMS, or methoxy (OMe). The particular X and B variables for each nucleoside and the % yield for each reaction are shown in Table 2.

TABLE 2

| Example | X | B | % Yield |
|---|---|---|---|
| 12 | OTBDMS | A(Bz) | 92 - HPLC |
| 13 | OTBDMS | C(Bz) | 93 - HPLC |

TABLE 1

| Example | Nucleoside | Base | Acid | Solvent | % Yield |
|---|---|---|---|---|---|
| 1 | Bz-DMT-dA | 2-Picoline | TFA | Methylacetate | 95 |
| 2 | Bz-DMT-dA | Sym-Collidine | TFA | Methylacetate | 89 |
| 3 | Bz-DMT-dA | Hünig Base | TFA | Methylacetate | 98 |
| 4 | Bz-DMT-dC | 2-Picoline | TFA | Isobutylacetate | 91 |
| 5 | Bz-DMT-dC | Sym-Collidine | TFA | Isobutylacetate | 95 |
| 6 | Bz-DMT-dC | Hünig Base | TFA | Isobutylacetate | 92 |
| 7 | iBu-DMT-dG | 2-Picoline | TFA | THF | 67 |
| 8 | iBu-DMT-dG | Hünig Base | TFA | THF | 92 |
| 9 | DMT-T | 2-Picoline | TFA | THF | 94 |
| 10 | DMT-T | Sym-Collidine | TFA | THF | 95 |
| 11 | DMT-T | Hünig Base | TFA | THF | 96 |

DMT = dimethoxytrityl;
Bz = benzoyl;
iBu = isobutyroyl

Examples 12–18

These Examples illustrate the phosphitylation of several protected nucleoside reagents with 2-Cyanoethyl-N,N,N',N'-tetraisopropylphosphordiamidite in the presence of a Hünig's Base-TFA activator according to the present invention.

Seven nucleoside reagents of the Formula III (below) were reacted with 2-Cyanoethyl-N,N,N',N'-tetraisopropylphosphordiamidite in the presence of a Hünig's Base-TFA activator according to the General Procedure for Examples 1–11, and the product yield calculated via one of two methods: (1) the resulting product mixture is run through an HPLC column using an appropriate eluent, and the area under the HPLC peaks used to determine the % yield of product in the mixture; or (2) the resulting product is purified on a short silica gel column using a methylacetate/toluene mixture (the concentration depending on the particular product being purified). The appropriate product fractions are concentrated under reduced pressure and solvent until an approximately 50% solution of the desired amidite is obtained. This solution is added to about 5 to 25 equivalents of petroleum ether to precipitate the product which is filtered TABLE 2-continued

| Example | X | B | % Yield |
|---|---|---|---|
| 14 | OMe | C(Bz) | 96 - HPLC |
| 15 | H | G(iBu) | 94 - HPLC |
| 16 | OTBDMS | G(iBu) | 92 - HPLC |
| 17 | H | T | 80 - isolated |
| 18 | OTBDMS | U | 85 - HPLC |

Example 19

This example illustrates the phosphitylation of $N^6$-benzoyl-5'-O-(4,4'-dimethoxytrityl)-2'-deoxyAdenosine (Bz-DMT-dA) with diisopropylethyl ammonium trifluoroacetate and 2-Cyanoethyl-N,N,N',N'-tetraisopropylphosphor-diamidite according of the present invention.

Diisopropylethylamine 6.4 g (49.4 mmol) is dissolved in 20 ml of dry THF in a reaction vessel. Trifluoroacetic acid 4.9 g (43.6 mmol) is added to the THF mixture at ambient temperature to form an activator solution for use in the following reaction step.

Bz-DMT-dA 30 g (45 mmol) is dissolved in 185 ml of dry THF in a reaction vessel and 50 ml of the THF is then distilled off under reduced pressure to form a reaction mixture. To the reaction mixture is added 14.7 g (47.2 mmol) of 2-Cyanoethyl-N,N,N',N'-tetraisopropylphosphordiamidite at ambient temperature. The activator solution prepared above is then added to the reaction mixture at ambient temperature with vigorous stirring. After 12 hours, the reaction mixture is diluted with 80 ml toluene and washed with 50 ml of water. The organic layer is separated and concentrated under reduced pressure. The resulting product is purified on a short silica gel column using methylacetate/toluene (80/20). The appropriate product fractions are concentrated under reduced pressure and solvent until an approximately 50% solution of 5'-O-Dimethoxytrityl-2'deoxyAdenosine-($N^6$-benzoyl)-3'-N,N-diisopropylamino-O-(2-cyanoethyl)phosphoramidite (PAm-Bz-DMT-dA) is obtained. The approximately 50% solution is added, with vigorous stirring (approximately 500–600 rpm), to a 1-L stainless steel reactor equipped with a mechanical stirrer and containing 500 ml hexane at ambient temperature. After 3 hours the resulting precipitate is filtered, washed with 50 ml hexane and dried yielding 32 g (83%) Pam-Bz-DMT-dA.

Example 20

This example illustrates the phosphitylation of N4-benzoyl-5'-O-(4,4'-dimethoxytrityl)-2'-deoxyCytidine (Bz-DMT-dC) with diisopropylethyl ammonium trifluoroacetate and 2-Cyanoethyl-N,N,N',N'-tetraisopropylphosphordiamidite according of the present invention.

Diisopropylethylamine 22.4 g (173 mmol) is dissolved in 30 ml of dry THF in a reaction vessel. Trifluoroacetic acid 18.4 g (164 mmol) is added to the THF mixture at ambient temperature to form an activator solution for use in the following reaction step.

Bz-DMT-dC 103 g (158.3 mmol) is dissolved in 450 ml of dry toluene in a reaction vessel and 100 ml of the toluene is then distilled off under reduced pressure to form a reaction mixture. To the reaction mixture is added 51.4 g (170.5 mmol) of 2-Cyanoethyl-N,N,N',N'-tetraisopropylphosphordiamidite at ambient temperature. The activator solution prepared above is then added to the reaction mixture at ambient temperature with vigorous stirring. After 12 hours, the reaction mixture is washed twice with 100 ml of aqueous ammonium acetate solution. The organic layer is separated and concentrated under reduced pressure. The resulting product is purified on a short silica gel column using methylacetate/toluene/triethylamine (100/30/2). The appropriate product fractions are concentrated under reduced pressure and solvent until an approximately 50% solution of 5'-O-Dimethoxytrityl-2'deoxyCytidine-(N-4-benzoyl)-3'-N,N-diisopropylamino-O-(2-cyanoethyl)phosphoramidite (PAm-Bz-DMT-dC) in toluene is obtained. Using a 3-L stainless steel reactor with mechanical stirrer this solution is added to a solution of 19 g of triethylamine in 1880 ml hexane with vigorous stirring (500–600 rpm) at 5° C. After 3 hours the resulting precipitate is filtered, washed with 100 ml hexane and dried yielding 112 g (85%) PAm-Bz-DMT-dC.

Comparative Examples 1–3

Three comparative phosphitylation reactions (C1–C3) comprising reacting a protected nucleoside reagent with 2-Cyanoethyl-N,N,N',N'-tetraisopropylphosphordiamidite in the presence of an pyridine-TFA activator were conducted, and the product yields of each calculated, according to the General Procedure described above for Examples 12–18. The various combinations of protected nucleoside, solvent, and yield for each of the 3 reactions are listed in Table 3. As illustrated by the yields in Table 3 (as compared to those of Tables 1 and 2), the yields associated with the methods of the present invention surprisingly tend to be at least as good, and in many embodiments, better, than those associated with comparable reactions using conventional activators comprising significantly less-hindered salts of unsubstituted pyridine.

TABLE 3

| Example | Nucleoside | Solvent | % Yield |
|---|---|---|---|
| C1 | Bz-DMT-dA | Methylacetate | 90 - isolated |
| C2 | Bz-DMT-dC | Isobutylacetate | 91 - isolated |
| C3 | DMT-T | THF | 95 - isolated |

Example 21

This Example illustrates the production of two oligonucleotide sequences (5'-ACGATGATGT-TCTCGGGCTTC-3' (SEQ ID NO: 1)) and (5'-TTTTTTTTTTC-3' (SEQ ID NO: 2)) using automated synthetic techniques according to the present invention.

An ABI 394 DNA Synthesizer was equipped with 4 synthesis columns comprising 0.2 micromole benzoyl-protected deoxycytosine on CPG (1000 angstroms) (from ABI). The Synthesizer was further equipped with 4 bottles, each comprising one of four 3'-O-phosphoramidites (based on dC, dA, dG, and T, respectively) to act as the sources of nucleoside phosphitylating agents in the reaction. The Synthesizer was further equipped with sources of the following solutions:

| | |
|---|---|
| Activator solution: | A 1.0 M Hunig's base/TFA complex (produced by combining 8.9 grams of diisopropyethylamine (Aldrich Biotech) with 8.9 grams of TFA in 43.0 grams acetonitrile (Honeywell Burdick and Jackson)); |
| Deblock - T: | 3% trichloroacetic acid in dichloromethane; |
| A Cap: | 10% acetic anhydride/10% pyridine/80% THF; |
| B Cap: | 10% N-methylimidazole/80% THF; and |
| Oxidation T: | 0.02 M iodine/2% water/20% pyridine/78% THF |

The nucleoside phosphitylation agents were reacted in sequence, in a fifty-fold excess per coupling, to achieve the desired oligonucleotides "fos-21" (5'-ACGATGATGT-TCTCGGGCTTC-3' (SEQ ID NO:1)) and "CT10" (5'-TTTTTTTTTTC-3' (SEQ ID NO: 2)). HPLC analysis was performed using an Agilent 1100 Series HPLC equipped with a PDA detector. Agilent ChemStation for LC 3D software was used to collect and analyze the data. The hplc column used was a Dionex DNAPak 100 (4×250 mm) column. A linear gradient with a 1.0 ml/min flow rate was used. The mobile phase was: B, 10 mM $NaClO_4$, 10 mM Tris-Cl pH, 8.3; D, 300 mM $NaClO_4$, 10 mM Tris pH, 8.3. The gradient program was as follows:

Oligonucleotide HPLC Analysis Gradient Program - 45 min.

| Time (min) | % B | % D |
|---|---|---|
| 0 | 100 | 0 |
| 5 | 75 | 25 |
| 30 | 40 | 60 |
| 35 | 0 | 100 |
| 40 | 100 | 0 |

The oligonucleotides were prepared for analysis at a concentration of 50 μg per ml in water. The OD260 peak crude DNA yield values were used to calculate the concentrations. Sample injections of 30 μl were made. Four samples for each oligonucleotide were tested. The average yields were measured to be about 42.7% for fos-21 and about 85.2% for CT-10.

Comparative Example 4

This Example illustrates the synthesis of two oligonucleotide sequences (5'-ACGATGATGTTCTCGGGCTTC-3' (SEQ ID NO: 1)) and (5'-TTTTTTTTTTC-3' (SEQ ID NO: 2)) using tetrazole and pyridine-TFA activators in automated synthesis.

The oligonucleotide sequences (5'-ACGATGATGT-TCTCGGGCTTC-3' (SEQ ID NO: 1)) and (5'-TTTTTTTTTTC-3' (SEQ ID NO: 2)) were each synthesized and tested as described in Example 22, except conventional activator solutions were used. In one experiment, both (5'-ACGATGATGTTCTCGGGCTTC-3' (SEQ ID NO: 1)) and (5'-TTTTTTTTTTC-3' (SEQ ID NO: 2)) were produced using tetrazole from Honeywell Burdick and Jackson, Inc. as an activator. In another experiment, (5'-ACGATGATGT-TCTCGGGCTTC-3' (SEQ ID NO: 1)) and (5'-TTTTTTTTTTC-3' (SEQ ID NO: 2)) were both produced using a pyridine-TFA activator as described in U.S. Pat. No. 6,274,725.

The average yield of (5'-ACGATGATGT-TCTCGGGCTTC-3' (SEQ ID NO: 1)) using tetrazole as an activator was 65.6% and using pyridine-TFA was 58.1%. The average yield of (5'-TTTTTTTTTTC-3' (SEQ ID NO: 2)) using tetrazole as an activator was 87.3% and using pyridine-TFA was 86.0%.

What is claimed is:

1. A method of producing a phosphitylated compound comprising the step of reacting a hydroxyl-containing compound with a phosphitylating agent in the presence of a phosphitylation activator selected from the group consisting of:

(1) acid-base complexes comprising a substituted pyridine or protonated pyridine moiety of Formula II

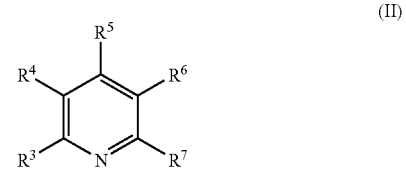

wherein $R^3$, $R^4$, $R^5$, $R^6$, and $R^7$ are independently hydrogen, $C_1$–$C_{10}$ alkyl, $C_3$–$C_{10}$ cycloalkyl, $C_6$–$C_{10}$ aryl, $C_7$–$C_{10}$ aralkyl, $C_1$–$C_{10}$ heteroalkyl, or $C_1$–$C_{10}$ heteroaryl, provided that at least one of said $R^3$, $R^4$, $R^5$, $R^6$, and $R^7$ is not hydrogen and $R^5$ is not a $C_2$–$C_{10}$ alkyl;

(2) zwitterionic amine complexes having pyridinyl and sulfonic acid substitutent moieties; and (3) combinations of two or more thereof.

2. The method of claim 1 wherein said phosphitylation activator is an acid-base complex base comprising a substituted pyridine or protonated pyridine moiety of Formula II.

3. The method of claim 2 wherein said moiety of Formula II is selected from the group consisting of dimethylaminopyridine (DMAP), 4-dimethylaminopyridium, methylpyndine, 2-picoline, 3-picoline, dimethylpyridine, 2,6-lutidine, trimethylpyridine, sym-collidine, tetramethylpyridine, pentamethylpyridine, and combinations of two or more thereof.

4. The method of claim 3 wherein said moiety of Formula II is 2-picoline or sym-collidine.

5. The method of claim 4 wherein said phosphitylation activator further comprises a moiety selected from the group consisting of trifluoroacetic acid, dichloroacetic acid, methane sulfonic acid, trifluoromethane sulfonic acid, non-aqueous hydrogen chloride, non-aqueous hydrogen bromide, non-aqueous hydrogen iodide, and $HBF_4$.

6. The method of claim 5 wherein said acid portion of said acid-base complex is trifluoroacetic acid.

7. The method of claim 1 wherein said phosphitylation activator is a zwitterionic amine complex.

8. The method of claim 7 wherein said zwitterionic amine complex is pyridineethansulfonic acid.

9. The method of claim 1 wherein said hydroxyl-containing compound is a nucleoside or an oligomer derived therefrom.

10. The method of claim 9 wherein said nucleoside is a 5'-O-protected nucleoside.

11. The method of claim 7 wherein said zwitterionic amine complex is 4-pyridiniumethylene sulfonic acid.

12. The method of purifying phosphitylated compounds comprising the steps of:
(a) providing a phosphitylated compound in solution comprising at least one phosphitylated oligonucleotide or phosphitylated nucleoside to be precipitated and a solution solvent selected from the group consisting of toluene, xylene, methyl acetate, ethyl acetate, propyl acetate, butyl acetates, and combinations of two or more thereof;

(b) contacting said compound solution with a precipitation solvent selected from the group consisting of petroleum ether, pentane, hexane, isohexane, heptane, isooctane, and mixtures of two or more thereof to precipitate said phosphitylated compound.

13. The method of claim 12 wherein said phosphitylated compounds are 3'-O-phosphoramidites.

14. The method of claim 12 wherein said solution solvent is toluene.

15. The method of claim 12 wherein said precipitation solvent is selected from the group consisting of petroleum ether, hexane, and combinations thereof.

16. The method of claim 12 wherein said contacting step comprises adding said phosphitylated compound and solution solvent to about 5 to about 25 equivalents by weight of said precipitation solvent.

17. The method of claim 16 wherein said contacting step comprises adding said phosphitylated compound and solution solvent to about 20 to about 25 equivalents by weight of said precipitation solvent.

18. The method of claim 12 wherein said precipitation solvent further comprises a triethylamine additive.

19. The method of claim 18 wherein said precipitation solvent comprises from about 0 to about 10 percent by weight of said additive.

20. The method of claim 18 wherein said precipitation solvent comprises from about 0 to about 5 percent by weight of said additive.

21. The method of claim 12 wherein said precipitation step is conducted at a temperature of about −20° C. to about 40° C.

22. The method of claim 21 wherein said temperature is from about 5° C. to about 25° C.

23. The method of claim 12 wherein said contacting step is conducted in a stainless steel vessel.

* * * * *

```
                        SEQUENCE LISTING

<160> NUMBER OF SEQ ID NOS: 2

<210> SEQ ID NO 1
<211> LENGTH: 21
<212> TYPE: DNA
<213> ORGANISM: human

<400> SEQUENCE: 1
acgatgatgt tctcgggctt c                                              21

<210> SEQ ID NO 2
<211> LENGTH: 11
<212> TYPE: DNA
<213> ORGANISM: artificial
<220> FEATURE:
<223> OTHER INFORMATION: synthetic oligonucleotide comprising ten T's
      and one C

<400> SEQUENCE: 2
tttttttttt c                                                         11
```